(12) United States Patent
Strong et al.

(10) Patent No.: US 10,883,987 B2
(45) Date of Patent: Jan. 5, 2021

(54) LATERAL FLOW DEVICE

(71) Applicant: Bio-Rad Laboratories, Inc., Hercules, CA (US)

(72) Inventors: William Strong, El Cerrito, CA (US); Clayton T. McKee, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 338 days.

(21) Appl. No.: 15/877,658

(22) Filed: Jan. 23, 2018

(65) Prior Publication Data

US 2018/0217140 A1    Aug. 2, 2018

Related U.S. Application Data

(60) Provisional application No. 62/451,501, filed on Jan. 27, 2017.

(51) Int. Cl.
| | | |
|---|---|---|
| *G01N 33/558* | (2006.01) | |
| *G01N 33/543* | (2006.01) | |
| *B01L 3/00* | (2006.01) | |

(52) U.S. Cl.
CPC ..... *G01N 33/558* (2013.01); *G01N 33/54386* (2013.01); *B01L 3/5023* (2013.01); *B01L 2200/0689* (2013.01); *B01L 2300/069* (2013.01); *B01L 2300/165* (2013.01); *B01L 2400/0406* (2013.01); *B01L 2400/0475* (2013.01)

(58) Field of Classification Search
None
See application file for complete search history.

(56) References Cited

U.S. PATENT DOCUMENTS

| | | |
|---|---|---|
| 4,981,785 A | 1/1991 | Nayak |
| 4,981,786 A | 1/1991 | Dafforn et al. |
| 5,198,193 A | 3/1993 | Bunce et al. |
| 5,710,005 A | 1/1998 | Rittenburg |
| 6,180,417 B1 | 1/2001 | Hajizadeh et al. |
| 8,507,260 B2 | 8/2013 | Alajem et al. |
| 8,603,832 B2 | 12/2013 | Whitesides et al. |
| 9,101,927 B2 | 8/2015 | Alajem et al. |
| 9,671,402 B2 | 6/2017 | McKee |
| 2001/0055542 A1 | 12/2001 | Chu |
| 2006/0246599 A1 | 11/2006 | Rosenstein et al. |
| 2007/0134811 A1 | 6/2007 | Takeuchi et al. |
| 2007/0196819 A1 | 8/2007 | Asberg et al. |
| 2007/0231923 A1 | 10/2007 | Cumberland et al. |
| 2010/0239459 A1 | 9/2010 | Alajem et al. |

(Continued)

FOREIGN PATENT DOCUMENTS

| | | |
|---|---|---|
| EP | 1 044 372 B1 | 9/2003 |
| EP | 2572189 A1 | 3/2013 |

(Continued)

OTHER PUBLICATIONS

Gong, et al., "Wax-bonding 3D microfluidic chips" Lab Chip, Mar. 29, 2010, vol. 10, pp. 2622-2627.

(Continued)

*Primary Examiner* — Rebecca M Giere
(74) *Attorney, Agent, or Firm* — Kilpatrick Townsend and Stockton LLP

(57) ABSTRACT

Lateral flow devices, methods and kits for performing lateral flow assays are provided.

20 Claims, 5 Drawing Sheets

(56) References Cited

U.S. PATENT DOCUMENTS

| | | |
|---|---|---|
| 2011/0189792 A1 | 8/2011 | Reinhartz et al. |
| 2012/0198684 A1 | 8/2012 | Carrilho et al. |
| 2013/0164193 A1* | 6/2013 | Semenov ............ B01L 3/50273 422/507 |
| 2015/0132742 A1 | 5/2015 | Thuo et al. |
| 2015/0241425 A1 | 8/2015 | McKee |
| 2016/0038935 A1 | 2/2016 | Alajem et al. |
| 2016/0274105 A1 | 9/2016 | Whitesides et al. |
| 2017/0191997 A1 | 7/2017 | McKee et al. |
| 2018/0024129 A1 | 1/2018 | Strong |
| 2018/0141040 A1 | 5/2018 | Strong et al. |

FOREIGN PATENT DOCUMENTS

| | | |
|---|---|---|
| WO | 2006/080021 A2 | 8/2006 |
| WO | 2010/007613 A1 | 1/2010 |
| WO | 2011/014673 A1 | 2/2011 |
| WO | 2013/095729 A1 | 6/2013 |
| WO | 2017/109775 A1 | 6/2017 |

OTHER PUBLICATIONS iBind TM Flex Western System User Guide; Catalog No. SFL2000, Revision Date Apr. 13, 2015; Publication No. MAN0010927, p. 8 and p. 20.
The International Search Report and Written Opinion from Application No. PCT/US2018/014789, dated Mar. 28, 2018; 9 pages.
Extended European Search Report in EP Application 18744679.4 dated Aug. 20, 2020; 9 pages.

* cited by examiner

LATERAL FLOW DEVICE

This application claims the benefit of U.S. Provisional Application 62/451,501 filed on Jan. 27, 2017 which is hereby incorporated by reference in its entirety.

BACKGROUND

Methods for detection of immobilized analytes are commonly employed in the biological sciences. For example, traditional blotting (e.g., Southern, northern, western, far western, eastern, vacuum, middle eastern, eastern-western, and far-eastern blotting, etc.) can be used to detect analytes immobilized on a substrate or membrane or in a matrix (e.g., in agarose or acrylamide). In general, such blotting techniques involve immobilization of the analyte(s) to be detected and contacting the analyte(s) with a binding agent (e.g., an antibody). Blotting also usually involves multiple washing steps and/or blocking steps between immobilization and final detection. Such washing and blocking steps consume a practitioner's limited time and/or reagents and can be a source of error and irreproducibility.

SUMMARY

Provided herein are lateral flow assay devices and methods of using such devices.

In an embodiment, the lateral flow device comprises a wicking pad composed of a porous material, the wicking pad having a planar region for contacting a substrate (e.g., a Western blot) comprising immobilized analytes (e.g., proteins); and wherein the wicking pad has a first end, a second end and two lateral edges; a support layer bonded to a first planar surface of the wicking pad; a top layer bonded to a second planar surface of the wicking pad, the top layer comprising two or more reservoirs spatially separated from each other, wherein the longitudinal axis of each reservoir is perpendicular to the lateral edges of the wicking pad, wherein each of the reservoirs is in fluid communication with the first end of the wicking pad, and wherein each of the reservoirs comprises an aperture through which a solution is released from the reservoir; and a pump comprising an absorbent pad located on the second end of the wicking pad.

In some embodiments, the wicking pad further comprises two or more zones separated from each other by a hydrophobic or impermeable barrier that is parallel to the lateral edges of the wicking pad. In some embodiments, the edges of the wicking pad are sealed with a water-tight material or with a heat seal. In certain embodiments, the water-tight material is selected from the group consisting of acrylic, wax, and photopolymers.

In certain embodiments, the top layer further comprises a first opening through which the substrate is contacted to the planar region of the wicking pad downstream from the reservoirs. In some embodiments, the top layer further comprises a second opening through which the pump is contacted to the second planar surface of the wicking pad downstream from the first opening. In some embodiments, the top layer comprises an opening through which the substrate is contacted to the planar region and through which the pump is contacted to the wicking pad downstream from the planar region.

In some embodiments, the aperture is a slot. In some embodiments, the reservoirs comprise two or more sets of reservoirs spatially separated from and adjacent to each other on the width axis of the lateral flow device. In some embodiments, each of the reservoirs spans a width of the wicking pad. In some embodiments, at least a first reservoir shares a wall with at least a second reservoir.

In some embodiments, the support layer and the top layer are formed from a liquid impermeable material. In certain embodiments, the liquid impermeable material is selected from the group consisting of polypropylene, polycarbonate, polystyrene, polyethylene terephthalate, and polyethylene terephthalate glycol-modified In some embodiments, the analytes are proteins.

Also provided are methods of performing lateral flow assays. In some embodiments, the method comprises providing a lateral flow device as described above or elsewhere herein; optionally applying running buffer to the wicking pad; applying a substrate comprising proteins (e.g., a Western blot) to the planar region for contacting the substrate; applying a different reagent solution to each of the reservoirs starting with a reservoir closest to the planar region for applying the substrate; and allowing lateral flow of the reagent solutions from the reservoirs to the pump such that each of the reagents in the reagent solutions is sequentially transported in the wicking pad and is contacted to the proteins on the substrate.

In some embodiments, the different reagent solutions are applied to the reservoirs sequentially or simultaneously.

In some embodiments, the allowing lateral flow step comprises allowing primary antibodies from a first reagent solution in a first reservoir to bind to target proteins, if present, on the substrate, followed by allowing a first wash solution from a second reagent solution in a second reservoir to remove unbound primary antibodies from the substrate. In some embodiments, the allowing lateral flow step further comprises allowing secondary antibodies or a secondary detection reagent from a third reagent solution in a third reservoir to contact the primary antibodies bound to target proteins, if present, on the substrate. In some embodiments, the allowing lateral flow step further comprises allowing a second wash solution from a fourth reagent solution in a fourth reservoir to remove unbound secondary antibodies from the substrate.

In some embodiments, the volume of the second wash solution is at least twice the volume of the third reagent solution having the secondary antibody. In certain embodiments, the method further comprises following binding of the primary antibodies to the target proteins if present, optionally following contact of secondary antibodies or secondary detection reagents to the primary antibodies, optionally removing the substrate, and detecting the binding of the primary antibodies to the target proteins if present.

In certain embodiments, the methods further comprise applying a substantially uniform pressure to the pump.

Also provided is a kit for performing lateral flow. In some embodiments, the kit comprises the lateral flow device as described above and elsewhere herein. In some embodiments, the kit includes a plurality of absorbent pads for use as a pump, all of which are described herein. In some embodiments, the kit includes reagents (e.g., binding agents including labeled primary antibody or primary and secondary antibodies, wash solution, and/or running buffer) provided as solutions to be applied to the reservoirs by the end-user. In certain embodiments, some or all of the reagents are dried onto the wicking pad in the portions of the wicking pad in fluid communication with each of the reservoirs of the device.

In some embodiments, the kit further includes running buffer for performing lateral flow and optionally includes blocking agents (e.g., bovine serum albumin, non-fat dried milk, or casein), surfactants (e.g., Tween 20 or Triton X-100), protein aggregation modifying agents as described herein, macromolecular crowding agents (e.g., dextran, polyethylene glycol and/or Ficoll), density agents and/or agents to promote even flow of reagents and/or promote reaction to molecules on the substrate and minimize background on the substrate. The additional agents can be provided in the kit as a solid or in liquid form. In some embodiments, the kit further includes instructions for carrying out the methods described herein.

BRIEF DESCRIPTION OF THE DRAWINGS

FIG. 3A shows the device with the substrate and pump in intimate contact with the wicking pad. FIGS. 3B and 3C show the device with no substrate or pump applied to the wicking pad.

DETAILED DESCRIPTION

Figure 1A:
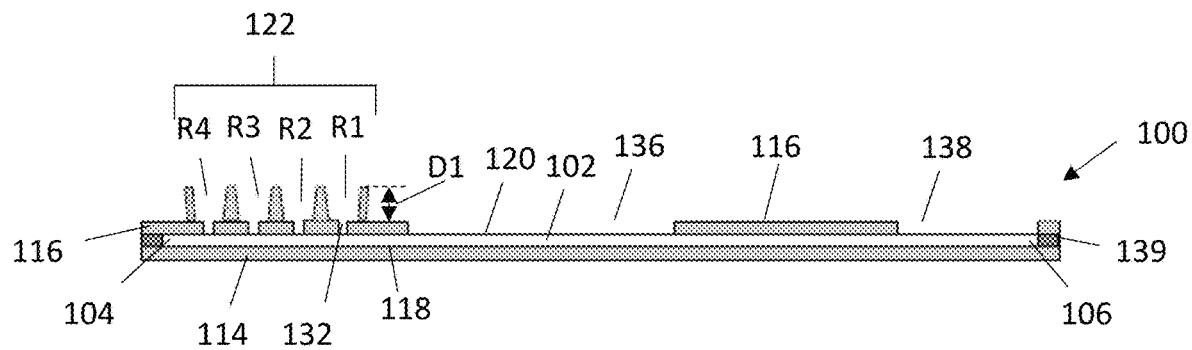
FIGS. 1A and 1B are schematic cross-sectional side and top views, respectively, of a lateral flow device according to an embodiment. The device includes four reservoirs that sequentially deliver reagent solutions to a wicking pad that is bonded to a support and to the four reservoirs. The device is shown with two openings in a top layer downstream from the reservoirs.
Figure 1B:
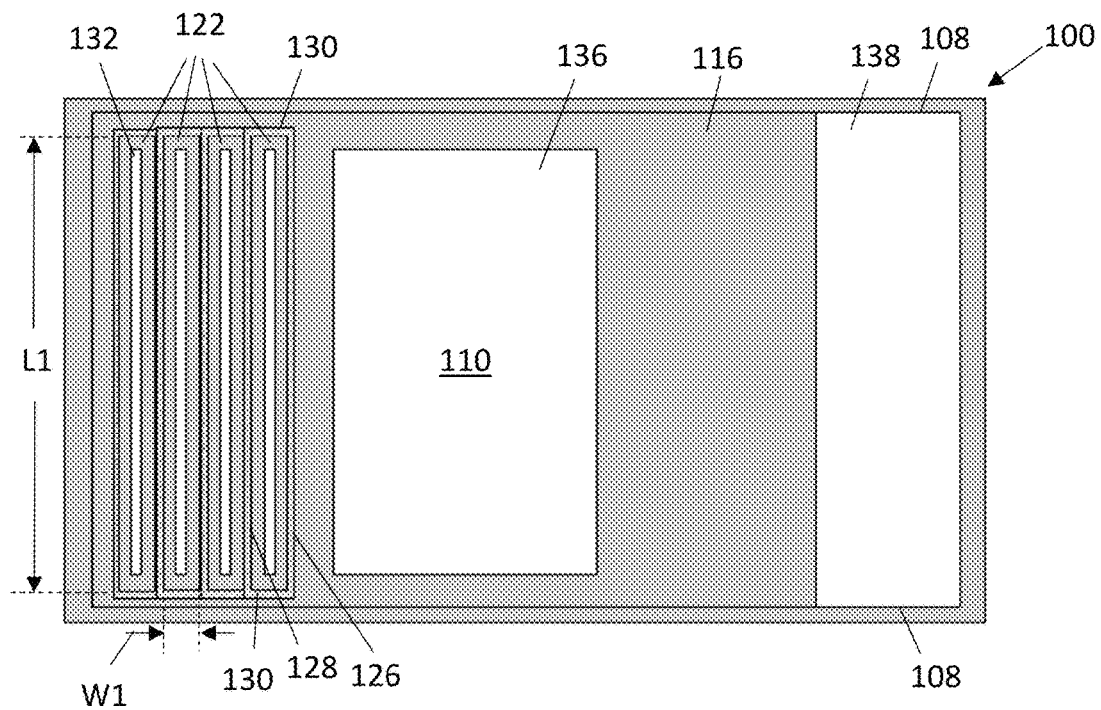
Figure 2A:
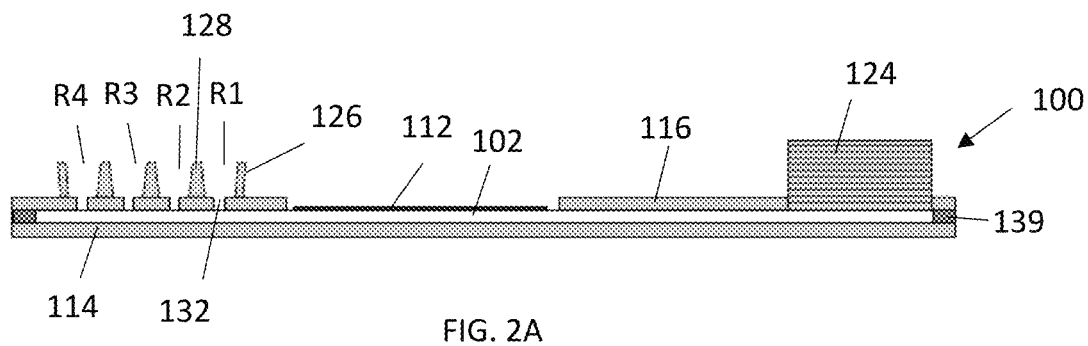
FIGS. 2A and 2B are schematic cross-sectional side and top views, respectively, of the device shown in FIGS. 1A and 1B with a substrate and a pump in intimate contact with the wicking pad. The substrate is applied to the wicking pad through the first opening and the pump is applied to the wicking pad through the second opening downstream from the first opening.
Figure 2B:
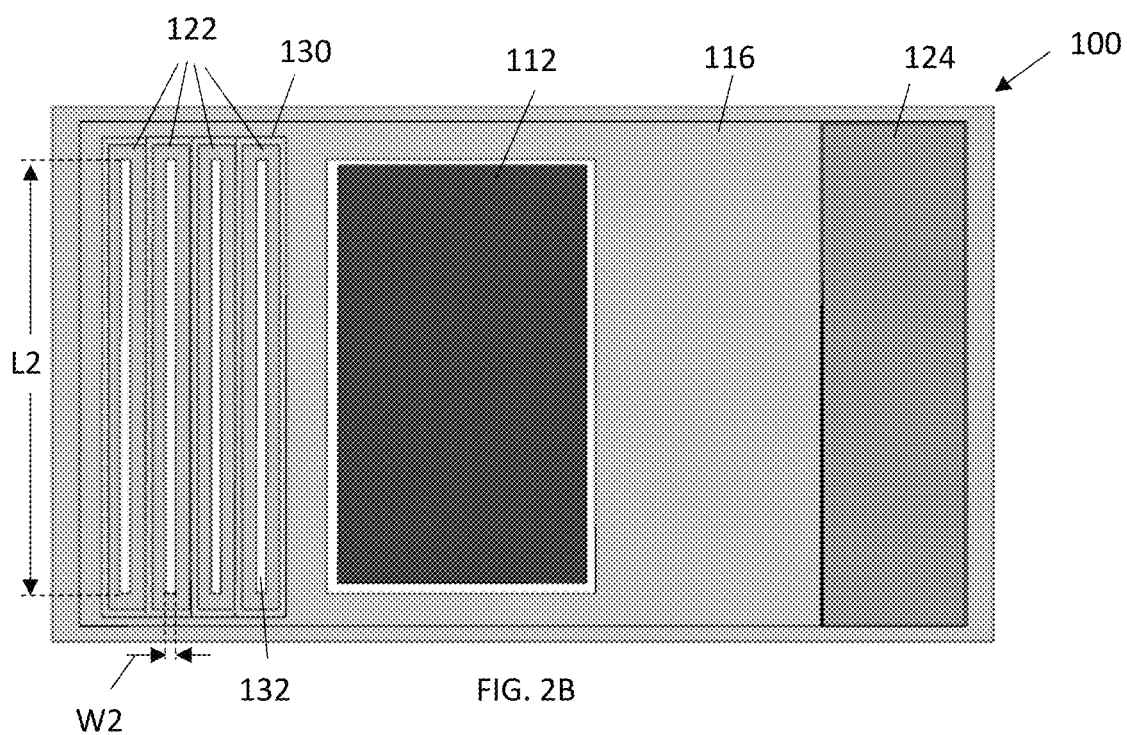
Figure 3A:
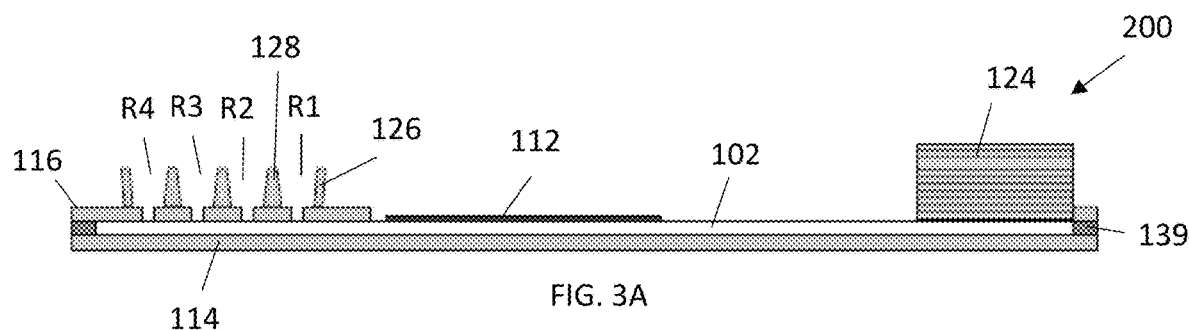
FIGS. 3A, 3B and 3C are schematic cross-sectional side and top views of a lateral flow device according to another embodiment. In this embodiment, the top layer partially covers the wicking pad, i.e., only the portion of the top layer having reservoirs covers and is bonded to the wicking pad. No top layer is present downstream from the reservoirs, i.e., in the planar region on which the substrate and pump are applied.
Figure 3B:
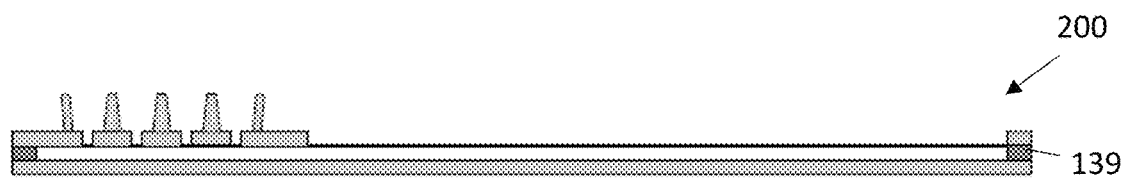
Figure 3C:
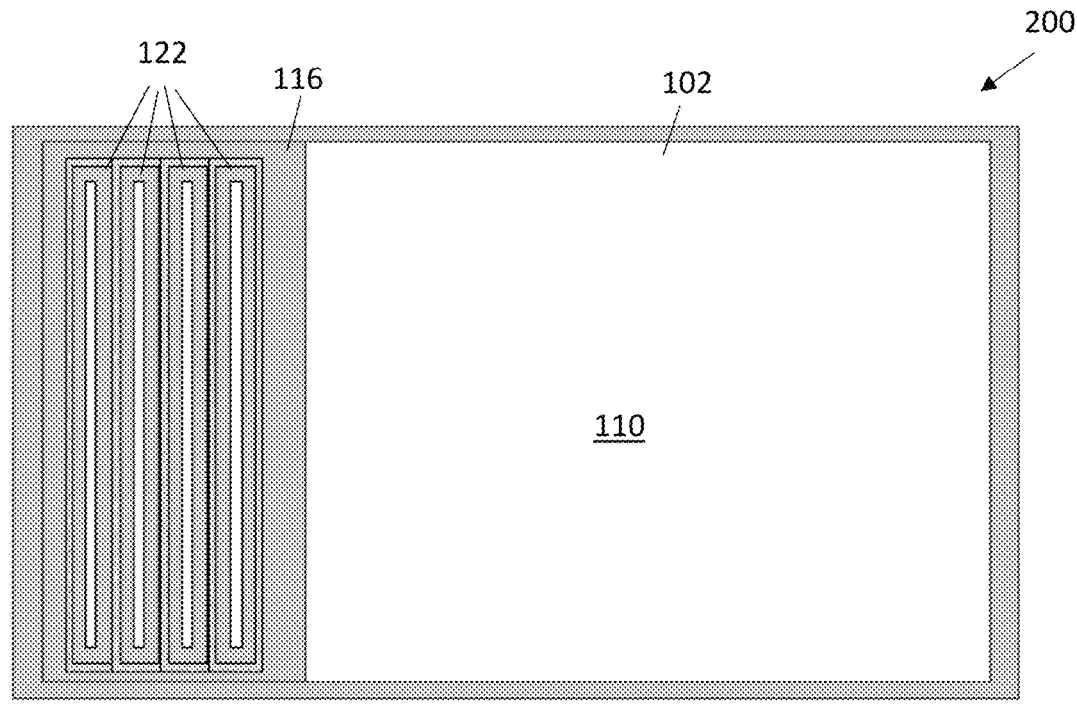
Figure 4:
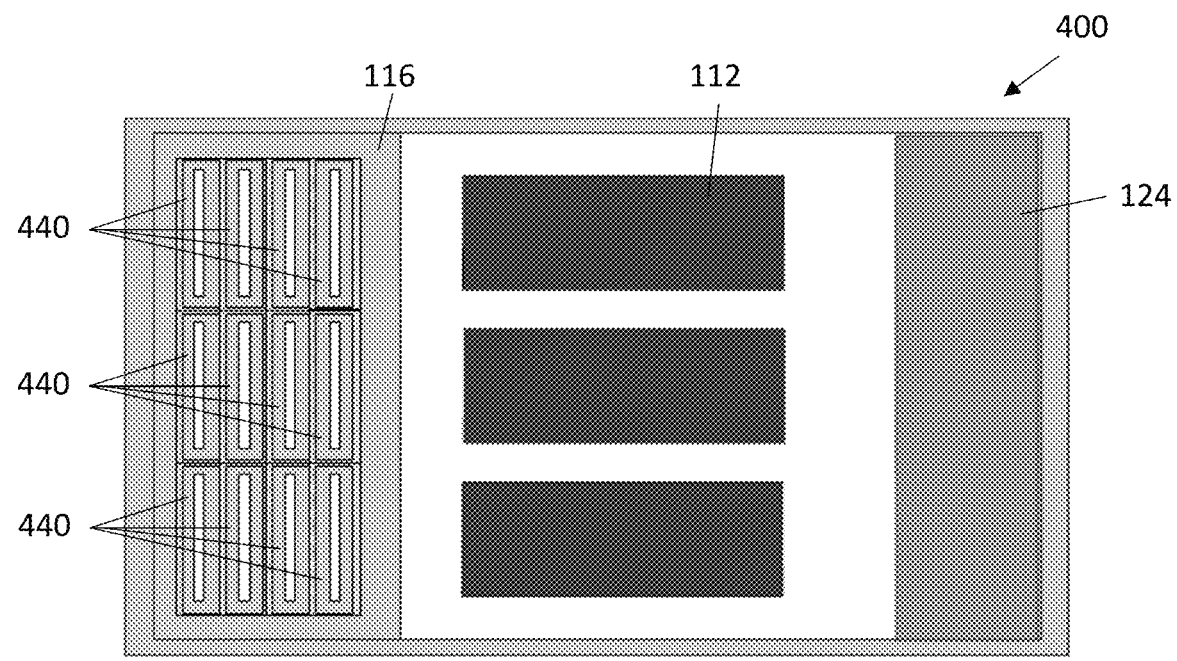
FIG. 4 is a schematic top view of a lateral flow device according to an embodiment having multiple sets of reservoirs such that multiple substrates can be analyzed at one time. The device is shown with multiple substrates in intimate contact with the wicking pad downstream from the multiple sets of reservoirs. The device is also shown with a pump in intimate contact with the wicking pad downstream from the substrates.

Described herein are lateral flow devices and methods of using such devices that allow for efficient lateral flow detection of analytes (e.g., proteins, nucleic acids) immobilized on substrates (e.g., western blot membranes) or the wicking pad (e.g., a diagnostic application) using specific binding agents (e.g., antibodies). The devices and methods described herein also allow for efficient lateral flow detection of analytes captured by specific binding agents immobilized on substrates. Lateral flow devices and methods of using such devices have been discovered that deliver different solutions (e.g., samples having one or more analytes, specific binding agents, running buffer, wash solutions) sequentially and hands-free to a wicking pad in intimate contact with a substrate having analytes or binding agents immobilized thereon. The solutions are delivered sequentially to the wicking pad from at least two reservoirs bonded to the wicking pad of the lateral flow devices. In some embodiments, the devices described herein can be configured in a single-use device, allowing for an affordable and simple assay format.

I. DEFINITIONS

The term "analyte" refers to a biological molecule, e.g., a protein, nucleic acid, polysaccharide, lipid, antigen, growth factor, hapten, etc., or a portion thereof. Analytes can be reversibly or irreversibly immobilized on a surface, such as a membrane or a wicking pad and detected as described herein.

The term "immobilized" or "embedded" interchangeably refers to reversibly or irreversibly immobilized molecules (e.g., analytes or binding agents). In some embodiments, reversibly immobilized molecules are immobilized in a manner that allows the molecules, or a portion thereof (e.g., at least 25%, 50%, 60%, 75%, 80% or more of the molecules), to be removed from their immobilized location without substantial denaturation or aggregation. For example, a molecule can be reversibly immobilized in or on an absorbent material (e.g., an absorbent pad) by contacting a solution containing the molecule with the absorbent material, thereby soaking up the solution and reversibly immobilizing the molecule. The reversibly immobilized molecule can then be removed by wicking the solution from the absorbent material, or from one region of the absorbent material to another. In some cases, a molecule can be reversibly immobilized on an absorbent material by contacting a solution containing the molecule with the absorbent material, thereby soaking up the solution, and then drying the solution-containing absorbent material. The reversibly immobilized molecule can then be removed by contacting the absorbent material with another solution of the same or a different composition, thereby solubilizing the reversibly immobilized molecule, and then wicking the solution from the absorbent material, or from one region of the absorbent material to another.

Irreversibly immobilized molecules (e.g., binding agents or analytes) are immobilized such that they are not removed, or not substantially removed, from their location under mild conditions (e.g., pH between about 4-9, temperature of between about 4-65° C.). Exemplary irreversibly immobilized molecules include protein analytes or binding agents bound to a nitrocellulose, polyvinylidene fluoride, nylon or polysulfone membrane by standard blotting techniques (e.g., electroblotting). Other exemplary irreversibly immobilized molecules include protein analytes or binding agents bound to glass, plastic (e.g., a microarray, a microfluidic chip, a glass histology slide or a plastic microtiter plate having wells with bound protein analytes therein), particles, nanoparticles or magnetic particles.

The term "binding agent" refers to a agent that specifically binds to a molecule such as an analyte. While antibodies are described in many contexts herein, it will be understood that other binding agents can be used instead of antibodies as preferred by the user. A wide variety of binding agents are known in the art, including antibodies, aptamers, affimers, lipocalins (e.g., anticalins), thioredoxin A, bilin binding protein, or proteins containing an ankyrin repeat, the Z domain of staphylococcal protein A, or a fibronectin type III domain. Other binding agents include, but are not limited to, biotin/streptavidin, chelating agents, chromatography resins, affinity tags, or functionalized beads, nanoparticles and magnetic particles.

The term "specifically bind" refers to a molecule (e.g., binding agent such as an antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, 100-fold, or 1000-fold or more greater affinity.

The term "antibody" refers to a polypeptide comprising a framework region from an immunoglobulin gene, or fragments thereof, that specifically bind and recognize an antigen, e.g., a particular analyte. Typically, the "variable region" contains the antigen-binding region of the antibody (or its functional equivalent) and is most critical in specificity and affinity of binding. See Paul, *Fundamental Immunology* (2003). Antibodies include for example chimeric, human, humanized antibodies, or single-chain antibodies.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

As used in this specification and the appended claims, the singular forms "a", "an", and "the" include plural referents unless the content clearly dictates otherwise. As used herein, the term "about" refers to the recited number and any value within 10% of the recited number. Thus, "about 5" refers to any value between 4.5 and 5.5, including 4.5 and 5.5.

II. DEVICES

FIGS. 1-5 illustrate embodiments of lateral flow devices for detecting analytes on a substrate, for detecting analytes bound to binding agents on a substrate, or for detecting analytes bound to binding agents on a wicking pad.

Referring to FIGS. 1A-2B, a lateral flow device 100 includes a wicking pad 102 having a first end 104, a second end 106, two lateral edges 108, and a planar region 110 for contacting a substrate 112 (e.g., a membrane) comprising immobilized analytes or proteins (e.g., a Western blot, a dot blot) to be detected. The lateral flow device 100 also includes a support layer 114 and a top layer 116. The support layer 114 is bonded to a first planar surface 118 of the wicking pad 102. The top layer 116 is bonded to a second planar surface 120 of the wicking pad 102. Thus, the wicking pad 102 is sandwiched (e.g., is laminated) between the support layer 114 and the top layer 116. The top layer 116 partially covers and is bonded to the wicking pad 102 and prevents evaporation of fluids during use of the lateral flow device 100. In some embodiments, the top layer 116 is bonded to the support layer 114 on the edges.

One end of the top layer 116 comprises two or more reservoirs 122 spatially separated from each other. In some embodiments, the longitudinal axis of each reservoir is perpendicular to the lateral edges 108 of the wicking pad 102 such that each reservoir is oriented perpendicular to the direction of lateral flow. The reservoirs 122 (e.g., R1, R2, R3, and R4) are located at or near the first end 104 of the wicking pad 102 upstream from the planar region 110 for contacting the substrate 112. As used herein, "near" is defined as no more than 10%, 20%, 30%, 40%, or 50% the length from the first end 104 of the wicking pad 102. Each of the reservoirs 122 is in fluid communication with the first end 104 of the wicking pad 102 (i.e., liquid, when present in the reservoirs 122, can flow from each of the reservoirs 122 into the wicking pad 102). The reservoirs 122 supply liquid (e.g., buffers and detection reagents) sequentially to the wicking pad 102 and into the planar region 110 for applying the substrate 112. The planar region 110 of the wicking pad 102 is located downstream from the reservoirs 122 and upstream from a pump 124 (i.e., between the reservoirs 122 and the pump 124).

As shown in FIGS. 1A-3C, the reservoirs 122 comprise one set of four reservoirs. In some embodiments (FIGS. 4 and 5), the reservoirs comprise two or more sets 440, 540 of reservoirs spatially separated from each other (e.g., separated by a wall or a distance) such that multiple substrates can be analyzed at one time. In some embodiments, the sets 440, 540 of reservoirs are adjacent to each other on the width axis of the lateral flow device 400, 500. The sets 440, 540 of reservoirs are arranged to run in parallel to each other in a side-by-side relationship. Each set of reservoirs is functionally independent of the adjacent set of reservoirs.

Referring again to FIGS. 1A-3C, each of the reservoirs 122 is bounded by a first wall 126 and a second wall 128 oriented perpendicular to the flow of liquid. Each of the reservoirs is further bounded by two end walls 130. In certain embodiments, the reservoirs share a wall. For example, the second wall of a first reservoir R1 can be the first wall of a second reservoir R2. The reservoirs 122 can be pre-molded during manufacture of the top layer 116 or can be manufactured separately and then bonded directly to the top layer 116.

The reservoirs 122 can be any size and shape. In some embodiments, each of the reservoirs 122 comprises a length L1, a width W1, and a depth D1. In some embodiments, each of the reservoirs is at least about 0.5, 1.0, 8.5, 13.5, 20 cm or more in at least one dimension. In some cases, the length L1 and the width W1 of each of the reservoirs 122 are at least about 2-fold, 3-fold, 5-fold, 10-fold, 100-fold or more larger than the depth D1. In some embodiments, each of the reservoirs is sized to match the width of the wicking pad 102 and has a length L1 that is at least about 3-fold, 4-fold, 5-fold, 6-fold, 8-fold, 10-fold, 13-fold, 17-fold, 20-fold, 27-fold or more larger than the width W1. Exemplary sizes of each reservoir include, but are not limited to, about 0.5 cm×0.5 cm, 0.5 cm×1 cm, 0.5 cm×8.5 cm, 1×3 cm, 3 cm×3 cm, 2.5 cm×about 8.5 cm, 1 cm×10 cm, 3 cm×10 cm, 2 cm×13.5 cm, 3×13.5 cm, 1 cm×15 cm, 3 cm×15 cm, or 3.5 cm×20 cm in width W1 and length L1, respectively. As used herein, the "width W1" is based on the direction of flow and is the shortest dimension. In some embodiments, each reservoir is 3 cm in width W1 by 10 cm in length L1. In some cases, each reagent reservoir is 1±0.5, 1, 2 or 3 cm in width W1 by 10±0.5 cm or 15±0.5 cm in length L1. In some cases, the depth D1 of at least one reservoir is about 0.5 cm, about 1 cm, about 2 cm, or about 3 cm.

Each of the reservoirs 122 comprises an aperture 132 (e.g., a slot) through which a solution is released from the reservoir and into the wicking pad 102. In embodiments in which the aperture 132 is a slot, the slot can have a width W2 (e.g., a short dimension) ranging from about 0.1 mm to about 5 mm and a length L2 (e.g., a long dimension) ranging from about 0.5 cm to about 20 cm. In some embodiments, the width W2 is 0.1 mm, 0.5 mm, 1 mm, 2 mm, 3 mm, 4 mm, or 5 mm. In certain embodiments, the length L2 is 8.5 cm, 9 cm, 9.5 cm, 13.5 cm, 15 cm, or 20 cm.

The volume of each of the reservoirs 122 can be determined by many factors including, but not limited to, the size and shape of the reservoirs 122 and the configuration of the lateral flow device 100. In some embodiments, each reservoir has a capacity of at least about 0.25 milliliters to about 30% milliliters. In some embodiments, the thickness of the top layer 116 defines the volume of the reservoir. In certain embodiments, the thickness of the top layer 116 is ⅜ inch or ¼ inch thick.

In some embodiments, the top layer 116 further comprises a first opening 136 through which the substrate is contacted to the planar region of the wicking pad downstream from the reservoirs (FIGS. 1A-2B). In certain embodiments, the top layer 116 further comprises a second opening 138 through which the pump is contacted to the second planar surface of the wicking pad downstream from the first opening 136. In some embodiments (FIGS. 3A-3C), the top layer 116 partially covers the wicking pad, i.e., only the reservoirs cover and are bonded to the wicking pad. In certain embodiments, no top layer is present downstream from the reservoirs, i.e., in the planar region on which the substrate and pump are applied. In some embodiments, the top layer 116 comprises an opening downstream from the reservoirs and the opening is of sufficient size to accommodate applying both the substrate 112 and the pump 124 to the wicking pad 102.

The pump 124 is located on or near the second end 106 of and in intimate contact with the wicking pad 102. The dry pump 124 acts as a drain by wicking the liquid from the reservoirs 122 through the wicking pad 102.

The planar region 110 of the wicking pad 102 can include drawings/markings or other indications for where a user should place the substrate 112 or where binding agents are immobilized in/on the wicking pad. Alternately, the drawing/markings can be on the support layer of the device.

The wicking pad 102 has a width, a length, and a height (e.g., a thickness). The wicking pad 102 can be any size and shape. In certain embodiments, at least a section (e.g., the planar region 110 for applying the substrate 112) of the wicking pad 102 is planar. In some cases, the length and the width of the wicking pad 102 are at least about 2-fold, 5-fold, 10-fold, 100-fold or more larger than the height (i.e., thickness).

Exemplary sizes for wicking pads include, without limitation, wicking pads that are at least about 0.25 cm, 0.5 cm, 1 cm, 2 cm, 3 cm, 4 cm, 5 cm, 6 cm, 7 cm, 8 cm, 10 cm, 12 cm, 15 cm, 20 cm, 25 cm, 30 cm or more in at least one dimension. In some cases, the wicking pad 102 is 20±0.5, 1, 2, 3, 4, 5, 6, 9 or 10 cm in length (in the direction of flow) by 10±0.5, 1, 2, 3, 4, 5, 6, 7, 8, or 9 cm in width.

The wicking pad 102 is an absorbent material. In some embodiments, the wicking pad 102 is configured to have a high solution capacity and a lateral flow rate. In some cases, the high solution capacity and lateral flow rate are provided by having a wicking pad 102 with substantial height (e.g., thickness). In some cases, the wicking pad 102 is about 10, 9, 8, 7, 6, 5, 4, 3, 2, 1, 0.75, 0.5, or about 0.2 mm thick. In some cases, the wicking pad 102 is between about 0.05 mm and about 0.5 mm thick.

Figure 5:
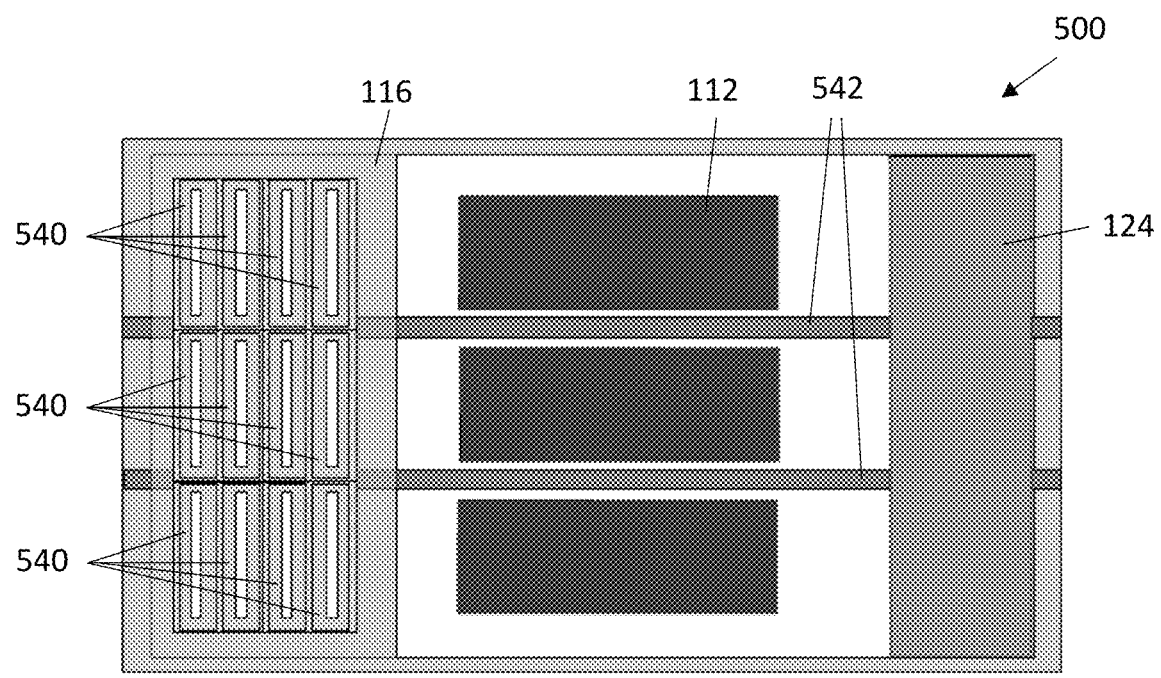
FIG. 5 is a schematic top view of a lateral flow device according to an embodiment having multiple sets of reservoirs such that multiple substrates can be analyzed at one time. In this embodiment, the wicking pad comprises two or more zones separated from each other by a hydrophobic or an impermeable barrier that is parallel to the lateral edges of the wicking pad. The device is shown with multiple substrates in intimate contact with the wicking pad downstream from the multiple sets of reservoirs and separated from each other by the barriers. The device is also shown with a pump in intimate contact with the wicking pad downstream from the substrates.

In some embodiments, the wicking pad 102 comprises one or more zones separated from each other by a hydrophobic or impermeable barrier 542 that is parallel to the lateral edges of the wicking pad (FIG. 5). The barriers 542 inhibit, eliminate, or substantially eliminate fluid communication (e.g., fluid flow) between adjacent zones in the wicking pad and allow for simultaneous processing of multiple substrates. Hydrophobic barriers include, but are not limited to, wax barriers, or barriers created by vapor or liquid phase silanization of the wicking pad. Exemplary materials from which impermeable barriers can be formed include, but are not limited to, wax, plastic, polymers, and resin. In some embodiments, each zone has its own pump 124.

The wax used to form the wax barriers can be any wax that is flowable at elevated temperatures and non-flowable at ambient temperature (e.g., about 20-25° C.). Examples are paraffin waxes, microcrystalline waxes, thermoset waxes, animal waxes such as beeswax, lanolin, and tallow, vegetable waxes such as soy, carnauba, candelilla and palm waxes, mineral waxes such as ceresin and montan waxes, petroleum waxes, and synthetic waxes such as ethylenic polymers, chlorinated naphthalenes, and Fischer-Tropsch waxes. Paraffin wax compositions may contain, in addition to n-paraffins and isoparaffins, minor amounts of cyclo-paraffins or olefins, or both. Waxes that become flowable, i.e., that have melting points, within the temperature range of from about 60° C. to about 150° C., or from about 75° C. to about 125° C., are among those that can be used. Wax formulations and compositions that behave in this manner are known to those of skill in the art.

The silanization reagent used to form hydrophobic barriers can be any silanization reagent that reacts with the porous substrate, or a portion thereof. For example, if the porous substrate contains cellulose, a silanization reagent that silanizes hydroxyl groups of the cellulose backbone can be utilized. Exemplary silanization reagents include, but are not limited to, trimethylchlorosilane, trimethylsilane, or hexamethyldisilazane. Silanization reagents further include triethoxysilanes (R—Si(C2HSO)3) where R is, for example, vinyl, methacrylol, aminopropyl, fluoroalkyl, or thioethyl. Other suitable silanization reagents will be readily apparent to those of skill in the art. Polymers can be reacted with the silane groups to create an impermeable barrier.

The wax or other barrier forming reagent (e.g., silanization reagent, or impermeable barrier) can be applied to one side or both sides of the porous substrate, although in most cases, application to one side will be sufficient, provided that the porous substrate penetrates, or is made to penetrate (e.g., by melting after application), the porous substrate to a degree sufficient to serve as a barrier to the flow of liquid. The barrier forming reagent can be applied as a liquid. The liquid can be applied by hand or other apparatus. In some cases, the liquid is sprayed or poured onto the porous substrate. Spraying can be accomplished with an inkjet printer or similar apparatus. In some cases, the liquid hardens after application to form an impermeable and/or hydrophobic barrier. Alternatively, the barrier forming reagent can be applied as a vapor. For example, a silanization reagent, wax, plastic, resin, or polymer can be applied as a vapor that condenses on the porous substrate or reacts with the porous substrate. Alternatively, the barrier forming reagent can be applied as a solid. For example, wax can be applied as a solid manually or in an automated or mechanized fashion. In some cases, the porous substrate is masked to protect regions from the barrier forming reagent, and the barrier forming reagent is contacted with the porous substrate.

Application of wax can be achieved by hand, either by the use of a common crayon or by a wax pen, or by a wax printer. Wax pens are known in the art and commonly include a housing having a reservoir to contain hot wax, a spout, and a handle. Application of the hot wax is achieved by tipping the housing to cause the liquefied wax to pass through the spout, and the housing is equipped with a valve to stop the flow of the wax at the terminus of a printed line.

Wax printers are likewise known in the art and commonly operated by thermal transfer printing using a print head that includes an array of very small heating elements that are software-controlled for independent activation to produce localized heating of the wax above its melting point to release the wax to the print medium. Commercially available examples of wax printers include the Phaser 8560DN (Fuji Xerox, Ltd., Japan), and the CALCOMP COLORMASTER PLUS thermal wax transfer printer (CalComp Graphics, LLC, Foothill Ranch, Calif., USA). Descriptions of wax printers and their use can be found in Kroon (Tektronix, Inc.), U.S. Pat. No. 5,957,593 (Sep. 28, 1999); Lin (Xerox Corporation), U.S. Pat. No. 8,206,664 (Jun. 26, 2012); Lu, Y., et al., "Rapid prototyping of paper-based microfluidics with wax for low-cost, portable bioassay," Electrophoresis 2009, 30, 1497-1500; and Carrilho, E., et al., "Understanding Wax Printing: A Simple Micropatterning Process for Paper-Based Microfluidics," Anal. Chem., 2009, 81 (16), 7091-7095. The width of a wax line as applied (prior to heating) can vary and is not critical to the present invention, provided that the amount of wax contained within the line is sufficient to penetrate the porous substrate and form a barrier to the lateral flow of fluid within the porous substrate.

In some embodiments, once applied, the wax can be made to penetrate the bulk thickness of the porous substrate to fill the pores or voids and form a lateral barrier to aqueous fluid flow by heating the wax above its melting point. In some cases, the amount of wax applied will be such that full penetration of the thickness of the wicking pad with the melted wax will occur while lateral flow of the melted wax (i.e., in directions parallel to the flat faces of the sheet) is minimal or at least limited to a small distance that is substantially uniform along the length of a line of applied wax so that the resulting area bordered by the wax barrier is known and controlled. The formation of the barrier in this manner can also be controlled by the degree of heating, including the temperature to which the wax is heated and the length of time that the heating is continued. Optimal temperatures and durations are readily determinable by routine trial and error, but in most cases serviceable results will be obtained by heating to at least 5° C. above the wax melting point, and in many cases from about 5 to about 50° C. above the melting point, or from about 10 to about 30° C. above the melting point. The most appropriate heating time will depend on the temperature, higher temperatures requiring less time. In general, heating times ranging from about fifteen seconds to about twenty minutes, or in many cases from about thirty seconds to about ten minutes, will provide useful results. Heating can be achieved by conventional means, including radiative heating, conductive heating, convective heating, impulse heating, and microwave heating. Effective results can be achieved with equipment as simple as a hot plate or a conventional oven.

Optimal widths for hydrophobic or impermeable barriers may vary with the dimensions of the area to be bordered by the barrier and with the thickness of the porous substrate and are readily determinable by routine testing. In most cases, the width will range from about 10 microns to about 5 mm, from about thirty microns to about 3 mm, from about 100 microns to about 1 mm, or from about 200 microns to about 5 mm, or 10 mm.

In some embodiments (e.g., a diagnostic assay embodiment), the wicking pad 102 has one or more reagents (e.g., binding agents such as antibodies) immobilized or embedded therein in one or more sections (e.g., in one or more sections downstream from the reservoirs). The embedded reagents are generally embedded or bound and dried into the wicking pad such that the reagents remain immobile during fluid flow or such that the reagents are immobile until contacted by an aqueous fluid front under lateral flow and are released at a user-defined event. The sections can be printed lines or spots of reagent.

The wicking pad 102 generally has a large surface area due to the presence of a plurality of pores or voids. The large surface area can increase the loading capacity of the wicking pad 102 for one or more reagents or one or more solutions containing a reagent. In some embodiments, the wicking pad 102 has a specific surface area of at least about 0.001 $m^2/g$, 0.02 $m^2/g$, 0.1 $m^2/g$, 0.5 $m^2/g$, 1 $m^2/g$, 10 $m^2/g$, or more as measured by standard techniques.

In some embodiments, the wicking pad 102 can have a particular pore size, a particular average pore size, or a particular pore size range. For example, the wicking pad 102 can contain 0.1 µm pores, 0.2 µm pores, 0.45 µm pores, or 1, 2, 4, 5, 6, 7, 8, 10, 15, 20 µm pores, or pores larger than about 20 µm. As another example, the wicking pad 102 can contain pores that average 0.1, 0.2, 0.45, 1, 2, 4, 5, 6, 7, 8, 10, 15, or 20 µm, or more in size. As another example, the wicking pad 102 can contain pores that range about 0.1-8 µm, 0.2-8 µm, 0.45-8 µm, 1-8 µm, 0.1-4 µm, 0.1-2 µm, 0.1-1 µm, 0.1-0.45 µm, 0.2-8 µm, 0.2-4 µm, 0.2-2 µm, 0.2-1 µm, 0.2-0.45 µm, 0.45-8 µm, 0.45-4 µm, 0.45-2 µm, 0.45-1 µm in size. In some cases, the wicking pad 102 can contain pores that are less than about 20 µm in size. For example, the wicking pad 102 can be composed of a material in which at least about 50%, 60%, 70%, 80%, 90% or more of the pores are less than about 20, 15, 10, or 5 µm in size. In some cases, the pores in the wicking pad 102 are large enough to contain one or more proteins of average size (e.g., about 1 nm). For example, the pores can be at least 1 nm in size, at least 5 nm in size, at least 10, 100, or 500 nm in size. Alternatively, at least 50%, 60%, 70%, 80%, 90% or more of the pores can be more than 1, 5, 10, 50, 100, or 500 nm in size. As used herein, pore size can be measured as a radius or a diameter. In some cases, the wicking pad 102 contains porous polyethylene, such as porous polyethylene having a pore size between 0.2 and 20 microns, or between 1 and 12 microns. The wicking pad 102 can have a different pore size in different regions of the pad. For example, the wicking pad 102 can have a lateral flow region that has a different pore size or pore size range. In some embodiments, pore size is chosen to control flow rate. For example, a larger pore size will allow for a faster flow rate. In some cases, the wicking pad (e.g, glass fiber or cellulose) contains voids which can be defined by the size of particles retained by the material and/or flow rate (e.g., time it takes for water to flow 4 centimeters).

In embodiments, the edges of the wicking pad 102 have a water-tight seal 139 (see FIGS. 1A, 2A, 3A, and 3B). The seal 139 is formed from water-tight material or with a heat seal to prevent liquid from leaking out of the edges during lateral flow. Exemplary water-tight materials that can be used to seal the edges of the wicking pad include, but are not limited to, acrylic (e.g., nail polish), wax, and photopolymers.

The wicking pad 102 can be treated or functionalized to minimize non-specific reagent binding, increase lateral flow, increase wicking, or to reduce protein aggregation. For example, the wicking pad 102, or a portion thereof, can be treated to alter the hydrophilicity or alter the hydrophobicity of the treated area. In some cases, altering the hydrophilicity or hydrophobicity of the wicking pad 102 can increase binding agent loading, decrease binding agent aggregation or denaturation, create mask regions in which binding agent is excluded from or not loaded, or direct flow of binding agents when the wicking pad is wet. In some cases, the wicking pad contains a protein aggregation modifying agent as described herein.

The wicking pad 102, and the pump are generally formed of a bibulous material and can be made out of, for example, natural fibers, synthetic fibers, glass fibers or blends thereof. Non-limiting examples include nitrocellulose, cotton, glass, and combinations thereof. There are many commercial materials available for diagnostic uses from vendors including, but not limited to, Ahlstrom, GE, PALL, Millipore, Sartorius, and S&S.

The pump is formed from material having a liquid absorbing capacity that is significantly greater than the wicking pad 102 and that allows a faster rate of fluid flow than through the wicking pad 102. In some embodiments, the pump is formed from one or more absorbent pads (e.g., a bibulous material).

The bibulous material can include, but is not limited to, polymer containing material. The polymer can be in the form of polymer beads, a polymer membrane, or a polymer monolith. In some cases, the polymer is cellulose. Cellulose containing pads include paper, cloth, woven, or non-woven cellulose substrates. Cloth pads include those containing a natural cellulose fiber such as cotton or wool. Paper pads include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose pads contains rayon. In some cases, the pad is paper, such as a variety of WHATMAN® paper.

The bibulous material can also include, but is not limited to, a sintered material. For example, the bibulous material can contain a sintered glass, a sintered polymer, or sintered metal, or a combination thereof. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

The bibulous material can also contain, but is not limited to, one or more non-cellulosic polymers, e.g. a synthetic polymer, a natural polymer, or a semisynthetic polymer. For example, the material can contain a polyester, such as polyglycolide, polylactic acid, polycaprolactone, polyethylene adipate, polyhydroxyalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a ($C_2$-$C_6$) monoolefin polymer, a vinylaromatic polymer, a vinylaminoaromatic polymer, a vinylhalide polymer, a ($C_1$-$C_6$) alkyl (meth) acrylate polymer, a(meth)acrylamide polymer, a vinyl pyrrolidone polymer, a vinyl pyridine polymer, a ($C_1$-$C_6$) hydroxyalkyl (meth)acrylate polymer, a (meth)acrylic acid polymer, an acrylamidomethylpropylsulfonic acid polymer, an N-hydroxy-containing ($C_1$-$C_6$) alkyl(meth)acrylamide polymer, acrylonitrile or a mixture of any of the foregoing.

The substrate 112 is generally planar in shape and can be, for example, a membrane formed of nitrocellulose, polyvinylidene fluoride, nylon, or polysulfone. Other materials from which the substrate 112 can be formed include, but are not limited to, glass, plastic, silicon, metal, and/or metal oxide that is bare or is functionalized with polymers. Plastic materials from which the substrate 112 can be formed include, but are not limited to, polyethylene terephthalate, polypropylene, polystyrene, and/or polycarbonate. Examples of polymers with which to functionalize the surface of substrates formed from plastic, glass, metal or metal oxide include glycidoxypropyltriethoxysilane, poly-L-lysine, polybrene, polyethylene glycol polymers, dextran polymer, aminopropylsilane, caroxysilane, hydrogels and polymer brushes, and/or self-assembled monolayers of e.g. functionalized alkyl thiols, dendrimers or oligonucleotides.

Exemplary bonding methods to bond the support layer and all or portions of the top layer to the wicking pad include, but are not limited to, bonding with an adhesive, thermal bonding, and organic solvent bonding with or without pressure. In embodiments using adhesive, the nature of the adhesive may affect the assay performance (i.e., flow characteristics, reagent stability) and can be optimized for the desired assay or application. In some embodiments, the adhesive may be part of the support layer of the device 100. Exemplary adhesives include, but are not limited to, spray adhesive, ultraviolet light curable adhesive, or pressure sensitive adhesive.

In some embodiments, the support layer and/or the top layer is formed from a liquid impermeable material (e.g., plastic) including, but not limited to, polyethylene terephthalate, polyethylene terephthalate glycol-modified, polypropylene, polystyrene, and polycarbonate. The support layer and/or the top layer can, for example, be vacuum or injection molded or otherwise constructed.

A. Exemplary Detection Reagents i. Binding Agents

Binding agents are described herein for detection of analytes. In some cases, the binding agents are antibodies (e.g., primary or secondary antibodies). Primary antibodies can be used to bind to an analyte. In some cases, the primary antibody is labeled, enabling detection of the primary antibody and subsequent detection of the analyte. In some cases, the primary antibody is detected by binding to a labeled secondary binding agent, such as a labeled secondary antibody. In some cases, tertiary binding agents are utilized to detect complexes containing the analyte and the primary and secondary binding agent.

Binding agents can be provided in one or more reagent solutions. The reagent solutions can contain one of more buffers, salts, density agents, or protein aggregation modifying agents as described herein. Density agents can be used to modulate the viscosity of the reagent solution which will modulate the rate of solution flow out of the reservoirs. Having a density agent in each of the reagent solutions can also enhance binding interactions between, e.g., the analytes immobilized on the substrate and the binding agents (e.g., antibodies). Examples of density agents include, but are not limited to, glycerol, sucrose, trehalose, dextran, and polyethylene glycol. The binding agent(s) can be stored in solution for at least about a day, three days, 7-10 days, at least about a month, two months, 3 months, six months, a year or longer.

Binding agents can also be provided on or in the wicking pad. For example, lines or spots of binding agents can be immobilized in/on the wicking pad downstream from the reservoir (e.g., in planar region 110). In some embodiments, a first binding agent is a reversibly immobilized labeled first primary antibody (e.g., a primary antibody conjugate) for detection, a second binding agent is an irreversibly immobilized unlabeled second primary antibody (e.g., a "test" primary antibody) for capture, and a third binding agent is a control antibody that binds to the first primary antibody. A control antibody can be used to assess assay validity. In certain embodiments, the labeled first primary antibody is paired with the second primary antibody and the two antibodies bind to different epitopes on the anlyte in such a way that the analyte, if present, is sandwiched in between the first primary antibody and second primary antibody during the lateral flow assay. In some embodiments, multiple matched pairs of first and second primary antibodies are immobilized on the wicking pad to allow for multiplex detection of analytes in the sample.

In some cases, a planar region of the wicking pad in fluid communication with fluid in one or more reservoirs contains one or more binding agents dried thereon. The dried binding agent(s) can be reconstituted by contacting the planar region of the wicking pad with an aqueous solution. In some cases, the aqueous reconstitution buffer can contain one or more re-wetting reagents including salts, buffers, or a protein aggregation modifying agent as described herein. In some cases, the binding agent (s) can be stored dry or substantially dry in the wicking pad for at least about a day, three days, 7-10 days, at least about a month, two months, 3 months, six months, a year or longer.

ii. Labels

Analytes can be detected by detecting a label that is linked to a binding agent. The label can be linked directly to the binding agent (e.g., by a covalent or other bond to the primary antibody) or the attachment can be indirect (e.g., using a chelator or linker molecule). The terms "label" and "detectable label" are used synonymously herein. In some embodiments, each label (e.g., a first label linked to a first binding agent, a second label linked to a second binding agent, etc.) generates a detectable signal and the signals (e.g., a first signal generated by the first label, a second signal generated by the second label, etc.) are distinguishable. In some embodiments, the two or more binding agent labels comprise the same type of agent (e.g., a first label that is a first fluorescent agent and a second label that is a second fluorescent agent). In some embodiments, the two or more binding agent labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, electrochemical labels and combinations thereof. In some embodiments, the label can include an optical agent such as a chromophore, fluorescent agent, phosphorescent agent, chemiluminescent agent, or an electrochemiluminescent agent. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include co-enzymes or co-factors that have a detectable absorbance. In some cases, a binding agent can be detected by detecting the intrinsic absorbance of a peptide bond at 220 nm or the composite amino acid absorbance at 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye, a DyLight dye, or an IRDye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.), Pierce Biotechnology, Inc. (Rockford, Ill.), and Licor Biosciences (Lincoln, Nebr.). In some embodiments, the optical agent is an intercalating dye. In some embodiments, 2, 3, 4, 5, or more binding agents are each labeled with an optical agent such as a fluorescent agent (e.g., a first binding agent labeled with a first fluorescent label, a second binding agent labeled with a second fluorescent label, etc.), and each binding agent that is labeled with an optical agent is detected by detecting a signal generated by the optical agent (e.g., a fluorescent signal generated by a fluorescent label). In some embodiments, the second fluorescent label quenches a fluorescent signal generated by the first fluorescent label. In some embodiments, the first and second fluorescent labels are members of a fluorescence resonance energy transfer (FRET) pair. The term "fluorescence resonance energy transfer" or "FRET" refers to a transfer of energy between at least two chromophores, a donor chromophore and an acceptor chromophore. Typically in FRET, if the donor and acceptor are in sufficiently close proximity, the donor transfers its energy to the acceptor when the donor is excited by light radiation with a suitable wavelength. The acceptor can re-emit the transferred energy in the form of light radiation with a different wavelength. Suitable FRET pairs (donor/acceptor) include, but are not limited to, EDANS/fluorescein, IAEDANS/fluorescein, fluorescein/tetramethylrhodamine, fluorescein/LC Red 640, fluorescein/Cy 5, fluorescein/Cy 5.5, and fluorescein/LC Red 705.

In some embodiments, all of the binding agents are labeled with an optical agent, and each optical agent-labeled binding agent is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}Ac$, $^{72}As$, $^{211}At$, $^{11}B$, $^{128}Ba$, $^{212}Bi$, $^{75}Br$, $^{77}Br$, $^{14}C$, $^{109}Cd$, $^{62}Cu$, $^{64}Cu$, $^{67}Cu$, $^{18}F$, $^{67}Ga$, $^{68}Ga$, $^{3}H$, $^{166}Ho$, $^{123}I$, $^{124}I$, $^{125}I$, $^{130}I$, $^{131}I$, $^{111}In$, $^{177}Lu$, $^{13}N$, $^{15}O$, $^{32}P$, $^{33}P$, $^{212}Pb$, $^{103}Pd$, $^{186}Re$, $^{188}Re$, $^{47}Sc$, $^{153}Sm$, $^{89}Sr$, $^{99m}Tc$, $^{88}Y$ and $^{90}Y$. In some embodiments, 2, 3, 4, 5, or more binding agents are each labeled with a radioisotope (e.g., a first binding agent labeled with a first radioisotope, a second binding agent labeled with a second radioisotope, etc.), and each binding agent that is labeled with a radioisotope is detected by detecting radioactivity generated by the radioisotope. For example, one binding agent can be labeled with a gamma emitter and one binding agent can be labeled with a beta emitter. Alternatively, the binding agents can be labeled with radionuclides that emit the same particle (e.g., alpha, beta, or gamma) at different energies, where the different energies are distinguishable. In some embodiments, all of the binding agents are labeled with a radioisotope and each labeled binding agent can be detected by detecting radioactivity generated by the radioisotope.

In some embodiments, the label is an enzyme, and the binding agent is detected by detecting a product generated by the enzyme. Examples of suitable enzymes include, but are not limited to, urease, alkaline phosphatase, (horseradish) hydrogen peroxidase (HRP), glucose oxidase, beta-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm, or a chemiluminescent substrate (e.g., Clarity from Bio-Rad Laboratories), which yields detectable light. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some cases, the enzyme acts on a fluorogenic substrate to generate a detectable fluorescent product. In some embodiments, 2, 3, 4, 5, or more binding agents are each labeled with an enzyme (e.g., a first binding agent labeled with a first enzyme, a second binding agent labeled with a second enzyme, etc.), and each binding agent that is labeled with an enzyme is detected by detecting a product generated by the enzyme. In some embodiments, all of the binding agents are labeled with an enzyme, and each enzyme-labeled binding agent is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), DNA-RNA hybrids, or artificial nucleic acid analogs (e.g., LNA, PNA). In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length. In some cases, the nucleic acid label is an amplified nucleic acid (e.g, by PCR or by isothermal polymerase extension). In some cases, a label or labels are incorporated into a nucleic acid label using a polymerase, reverse transcriptase, ligase, or other enzymes that act on nucleic acids (e.g., fluorescently modified nucleotides, biotin-nucleotides, digoxigenin-nucleotides, hapten nucleotides). In some embodiments, the nucleic acid label is ligated to another label (e.g., a nucleic acid) to create a detectable product (e.g, proximity ligation assays).

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled binding agent. The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al., "Digital RNA sequencing minimizes sequence-dependent bias and amplification noise with optimized single-molecule barcodes", PNAS 2012 Jan 24;109(4):1347-52; and Smith, AM et al., "Highly-multiplexed barcode sequencing: an efficient method for parallel analysis of pooled samples", Nucleic Acids Research 2010 Jul;38(13):e142

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding agents such as proteins (e.g., antibodies) are well known. For example, a review of common protein labeling techniques can be found in *Biochemical Techniques: Theory and Practice,* John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J. Biolumin Chemilumin* 1989, 4:140-148.

B. Protein Aggregation Modifying Agents

Described herein are protein aggregation modifying agents. Protein aggregation modifying agents can be utilized to reduce or eliminate aggregation or denaturation of binding agents, such as proteins (e.g., antibodies), stored in or delivered from a reagent solution, or the wicking pad 102. For example, protein aggregation modifying agents can be utilized to reduce or eliminate aggregation or denaturation of primary antibodies stored in/ delivered from the reagent solutions or the wicking pad 102. In some cases, protein aggregation modifying agents can be utilized to facilitate lateral flow of binding agents in the planar region 110 of the wicking pad 102 or to reduce background on the substrate 112.

In some cases, protein aggregation modifying agents that act to displace proteins from the air-water interface and thereby protect them from denaturation and aggregation are particularly effective in reducing the aggregation of binding agents immobilized on the wicking pad 102. In other cases, the protein aggregation modifying agent directly affects the stability of the binding agent by binding to the binding agent and/or stabilizing the binding agent. In other cases, the protein aggregation modifying agent acts to shift the equilibrium away from a denatured or unfolded state and thus reduce aggregation. For example, in some cases, the interaction between the protein aggregation modifying agent and the binding agent is thermodynamically disfavored due to strong repulsion between an amide backbone of the binding agent and the protein aggregation modifying agent. Thus, unfolding of the binding agent in the presence of the protein aggregation modifying agent is disfavored because unfolding exposes more amide backbone surface to the protein aggregation modifying agent.

Protein aggregation modifying agents can be one or more of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, or a chaotropic agent.

Cyclodextrins can be, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, or succinyl-(2-hydroxypropyl)-γ-cyclodextrin. Cyclodextrins can also be a cyclodextrin polymer containing one or more of the foregoing cyclodextrin molecules. Additional cyclodextrins are known in the art, and include, e.g. those described on the world wide web at cyclodextrin.com. Exemplary concentrations of cyclodextrins are, without limitation, about 1 mM, 2 mM, 2.5 mM, 5 mM, 7.5 mM, 10 mM, 15 mM, 20 mM, 25 mM, 50 mM, 75 mM, or 100 mM.

Non-ionic surfactants can be polyethylene-sorbitan-fatty acid esters, polyethylene-polypropylene glycols or polyoxyethylene-stearates. Polyethylene-sorbitan-fatty acid esters can be polyethylene(20)-sorbitan-esters (Tween 20™) or polyoxyethylene(20)-sorbitanmonooleate (Tween 80™). Polyethylene-polypropylene glycols can be polyoxypropylene-polyoxyethylene block co-polymers such as those sold under the names Pluronic® or Poloxamer™ Polyoxyethylene-stearates can be, for example, those sold under the trademark Myrj™ Exemplary, polyoxyethylene monolauryl ethers include those sold under the trademark Brij™ e.g., Brij-35. Exemplary concentrations of non-ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Ionic surfactants can be anionic surfactants or cationic surfactants. Anionic surfactants useful in the present invention can be, but are not limited to, soaps including alkali soaps, such as sodium, potassium or ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride or quarternary ammonium compounds such as benzalkonium chloride. Ionic surfactants can include the sodium, potassium or ammonium salts of alkyl sulfates, such as sodium dodecyl sulfate or sodium octyl sulfate. Exemplary concentrations of ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can be a sulfonate, as in CHAPS (3-[(3-Cholamidopropyl)dimethylammonio]-1-propanesulfonate). Other anionic groups are sultaines illustrated by cocamidopropyl hydroxysultaine or betaines, e.g., cocamidoethyl betaine, cocamidopropyl betaine, or lauramidopropyl betaine. Exemplary concentrations of zwitterionic surfactants are, without limitation, about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. Exemplary NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, or Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can be simple sugars such as sucrose, mannitol, sorbitol, inositol, xylitol, erythritol, glucose, galactose, raffinose, or trehalose. Polyols can also be polysaccharides such as dextran, starch, hydroxyethyl starch, or polymers containing one or more of the simple sugars described herein. Glycerol, ethylene glycol, polyethylene glycol, pentaerythritol propoxylate, and pentaerythritol propoxylate, and combinations thereof are also exemplary polyols.

Organic solvents can be, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, or dimethyl sulfoxide.

Aggregation modifying proteins can be proteins known in the art to inhibit denaturation, unfolding, or aggregation of one or more proteins. Exemplary aggregation modifying proteins include, but are not limited to, albumins, protein chaperones, and heat shock proteins. Albumins are proteins that are water-soluble, are moderately soluble in concentrated salt solutions, and experience heat denaturation. Exemplary albumins include serum albumins (e.g., bovine, horse, or human serum albumin) or egg albumin (e.g., hen egg-white albumin). Other exemplary aggregation modifying proteins include casein, gelatin, ubiquitin, lysozyme, or late embryogenesis abundant (LEA) proteins. LEA proteins include LEA I, LEA II, LEA III, LEA IV, LEA V, or atypical LEA proteins. LEA proteins are known in the art and described, e.g., in Goyal K., et al., Biochemical Journal 288(pt. 1), 151-57, (2005).

Protein aggregation modifying agents can also be amino acids. In some cases, the amino acids can serve an oxido-reduction function to maintain an appropriate oxidative potential for the protein immobilized on the substrate 112. Suitable oxido-reductive amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to reduce protein aggregation. Oxido-reductants other than cysteine and cystine, can be used to optimize the reduction potential in the substrate 112 onto which the protein is immobilized. Exemplary oxido-reductants include mercaptoethanol, dithiothreitol, dithioerythritol, tris(2-carboxyethyl)phosphine, glutathione, glutathione disulfide, and oxidized derivatives thereof, as well as $Cu^{2+}$.

Protein aggregation modifying agents can also include lyoprotectants, cryoprotectants, or chaotropic agents. In some cases, the protein aggregation modifying agent is a chaotrope such as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other protein aggregation modifying agents include trimethylamine N-oxide.

Protein aggregation modifying agents can be salts. Exemplary salts include, but not limited to, the sodium, potassium, magnesium, or calcium salts of chloride, sulfate, or phosphate. Protein aggregation modifying agents can also be buffering agents. Exemplary buffering agents include, but are not limited to, tris (hydroxymethyl) amino methene (TRIS), TAPSO, MES, HEPES, PIPES, CAPS, CAPSO, MOPS, MOPSO, or sodium or potassium phosphate, carbonate, bicarbonate, citrate, acetate, or borate buffers.

The protein aggregation modifying agents can be provided in any suitable concentration. In some cases, the protein is provided as an aqueous solution containing binding agent and protein aggregation modifying agents. In such cases, the solution can be contacted with the wicking layer and, optionally, dried. Exemplary concentrations of protein aggregation modifying agents in the aqueous binding agent solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 µM, 5 µM, 10 µM, 25 µM, 50 µM, 75 µM, 100 µM, 150 µM, 200 µM, 300 µM, 500 µM, 750 µM, 1 mM, 5 mM, 10 mM, 25 mM, 50 mM, 100 mM, 150 mM, 200 mM, 300 mM, 500 mM, and 1M.

In some cases, the protein aggregation modifying agents are provided in the reagent solution. Exemplary compositions containing a protein aggregation modifying agent contain about 0.001%, 0.005%, 0.01%, 0.05%, 0.1%, 0.5%, 1%, 2%, 3%, 4%, 5%, or about 10%, 20%, or about 25% by weight of one or more protein aggregation modifying agents.

Protein aggregation modifying agents can be provided in any suitable combination. For example, in some cases, 1, 2, 3, 4, 5, 6, 7, 8, 9, 10 or more of the foregoing protein aggregation modifying agents can be utilized to reduce aggregation of a binding agent reversibly immobilized on the wicking pad. In some cases, prior to contacting the wicking pad with the binding agent solution, the wicking pad contains a protein aggregation modifying agent, and the binding agent solution contains the same, or a different, protein aggregation modifying agent. In some cases, prior to contacting the wicking pad with the binding agent solution, the wicking pad contains a protein aggregation modifying agent, and the binding agent solution does not contain a protein aggregation modifying agent. In some cases, prior to contacting the wicking pad with the binding agent solution, the binding agent solution contains a protein aggregation modifying agent and the wicking pad, or the region to be contacted, does not.

METHODS

Provided are methods of performing a lateral flow assay using the devices described herein. In an embodiment, the method comprises contacting a substrate 112 (e.g., a Western blot) having immobilized analytes or binding agent(s) within or on the wicking pad 102, which can be supplied pre-moistened or can be pre-moistened by the user with, for example, lateral flow buffer. In some embodiments (FIGS. 1A-5), the substrate 112 is placed face down on the wicking pad 102 through an opening in the top layer 116 downstream from the reservoirs and upstream from the pump 124 (e.g., between the reservoirs and the pump or in the planar region 110 of the wicking pad 102).

A different reagent solution is next applied to each of the reservoirs starting with a first reservoir R1 closest to the region 110 for contacting the substrate 112. The reagent solutions can be applied to the reservoirs sequentially or simultaneously. The reagent solutions can also be applied to the reservoirs in any order. In an embodiment, four different reagent solutions (e.g., primary antibody, first wash solution, secondary antibodies or secondary detection reagents, and second wash solution) are applied to the reservoirs. In embodiments having two or more sets of reservoirs (FIGS. 4 and 5), a different or the same set of four reagent solutions is applied to each set of reservoirs, depending on the analytes or binding agents immobilized on the substrate 112.

In some embodiments, a first reagent solution having labeled primary antibody is applied to a first reservoir R1 and a second reagent solution having a first wash solution is applied to a second reservoir R2. In certain embodiments, four different reagent solutions are applied to the reservoirs in the following order: the first reagent solution having primary antibody is applied to the first reservoir R1, the second reagent solution having a first wash solution is applied to the second reservoir R2, a third reagent solution having a secondary antibody or a secondary detection reagent is applied to a third reservoir R3, and a fourth reagent solution having a second wash solution is applied to a fourth reservoir R4. In some embodiments, the reagent solution applied to the reservoir has at least twice the volume of another reagent solution. For example, the volume of the second wash solution in the fourth reservoir R4 can be at least twice the volume of the secondary antibody in the third reservoir R3. In some embodiments, the fourth reagent solution having the second wash solution is omitted to allow the secondary antibody or secondary detection reagent in the third reservoir R3 more time to bind to the primary antibody.

In an embodiment in which the substrate has immobilized binding agents thereon, a sample with an analyte is applied to the first reservoir R1, a first wash solution is applied to the second reservoir R2, a secondary detection reagent is applied to the third reservoir R3 and, if needed, a second wash solution is applied to the fourth reservoir R4.

In some embodiments in which there is no substrate 112 and in which binding agents are immobilized in lines or spots on a planar region 110 of the wicking pad 102 downstream from the reservoirs, a different solution (e.g., a sample or a reagent solution) is applied to at least two of the reservoirs. In an embodiment in which a line of labeled reversibly immobilized first primary antibodies (e.g, a primary antibody conjugate), a line of unlabeled irreversibly immobilized second primary antibodies (e.g., test primary antibodies), and a line of irreversibly immobilized control antibodies that bind to the first primary antibodies is printed on the planar region 110 of the wicking pad 102, a sample having one or more analytes and optionally a control protein is applied to the first reservoir R1 and a wash solution (e.g., lateral flow buffer) is applied to the second reservoir R2. In some embodiments in which an unlabeled second primary antibody and a control antibody are irreversibly immobilized on the planar region 110 of the wicking pad 102, a detection reagent (e.g., labeled primary antibody) is applied to the third reservoir R3 and, if needed, a second wash solution is applied to the fourth reservoir R4.

In an embodiment in which analytes are immobilized in lines or spots on the planar region 110 of the wicking pad 102 downstream from the reservoirs, a labeled primary antibody is applied to the first reservoir R1 and a first wash solution is applied to the second reservoir R2. If needed, a secondary detection reagent is applied to the third reservoir R3 and a second wash solution is applied to the fourth reservoir R4.

The reagent solutions and/or sample are then allowed to flow sequentially from the reservoirs onto the planar region 110 of the wicking pad 102. In some cases, the lateral flow (e.g., the progress) of each of the reagent solutions out of the reservoirs 122 and into/through the wicking pad 102 is monitored visually with one or more dyes or indicators in each of the reagent solutions.

In embodiments having analytes immobilized on the substrate 112, the reagent solutions are pulled by wicking from the reservoirs into the wicking pad and to the dry pump, carrying the reagents (e.g., the primary antibody, the first wash solution, and if needed, secondary antibodies and the second wash solution) in the reagent solutions sequentially by lateral flow into contact with the substrate 112 having proteins or analytes immobilized thereon. The primary antibodies in the first reagent solution are transported in the wicking pad 102, contact the proteins or analytes on the substrate 112, and bind to the target proteins or analytes, if present, on the substrate 112. In some embodiments, lateral flow of the reagent solutions/lateral flow buffer from the reservoirs to the pump further allows the first wash solution in the second reagent solution to be transported in the wicking pad 102 such that unbound primary antibodies are removed from the substrate 112. In certain embodiments, lateral flow of the reagent solutions/ lateral flow buffer from the reservoirs to the pump further allows the secondary antibodies or a secondary detection reagent in the third reagent solution to be transported in the wicking pad 102 and to contact the primary antibodies bound to target proteins, if present, on the substrate 112. In some embodiments, lateral flow of the reagent solutions/lateral flow buffer from the reservoirs to the pump further allows the second wash solution in the fourth reagent solution to be transported in the wicking pad 102 such that unbound secondary antibodies are removed from the substrate 112. In some embodiments, the volume of the second wash solution applied to and transported in the wicking pad 102 is twice the volume of secondary antibody applied to and transported in the wicking pad 102.

In embodiments in which binding agents are immobilized on the substrate 112, the sample and reagent solutions are pulled by wicking from the reservoirs into the wicking pad and to the dry pump, carrying the analytes (and optional control protein) in the sample and the reagents (e.g., the first wash solution, the secondary detection reagent and, if needed, the second wash solution) in the reagent solutions sequentially by lateral flow into contact with the substrate 112. In some embodiments, the sample is a biological sample. Biological samples can be obtained from any biological organism, e.g., an animal, plant, fungus, bacterial, or any other organism, In some embodiments, the biological sample is from an animal, eg., a mammal (e,g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, stool, or urine. In some embodiments, the sample includes a positive control protein for assessing assay validity or for normalizing the test signal across a multiplicity of different antibody zones.

In embodiments in which binding agents are immobilized on the region 110 of the wicking pad downstream from the reservoirs, the sample and reagent solutions are pulled by wicking from the reservoirs into the wicking pad and to the dry pump, carrying the analytes in the sample and the reagents (e.g., the first wash solution and, if needed, the secondary detection reagent and the second wash solution) in the reagent solutions sequentially by lateral flow into contact with the region 110.

In some embodiments, before or after initiating lateral flow and during lateral flow, a substantially uniform pressure is applied to the pump to improve contact of the pump with the wicking pad 102. For example, a weight can be placed on top of the pump to urge the pump toward the wicking pad 102.

In some embodiments, a cover can be placed onto the device once the reagent solutions have been applied to the reservoirs to minimize evaporation and to apply even pressure to the pump 124. The cover can be placed loosely on top of the device and then the device with the cover can be placed into a drawer-like container that slides into a box. Prior to placing the cover on the device or in place of the cover, a sponge can be placed on the pump to aide in applying even pressure to the pump. The process requires minimal user interaction with the consumable.

In some embodiments having a substrate, during lateral flow, the binding of primary antibodies to the target proteins (and optionally contact of secondary antibodies or secondary detection reagents to the primary antibody) is followed visually or by using a detector. In some embodiments, the substrate (s) is/are removed from the lateral flow device 100 and the binding of the primary antibodies to the target proteins, if present, is detected. In some embodiments, the antibody binding to the target protein is visualized and/or detected through the use of detectable moieties and/or labels as described herein. Suitable labels and/or moieties are detected by spectroscopic, photochemical, biochemical, immunochemical, isotopic, electrical, optical, chemical, or mass spectrometric techniques.

In an embodiment in which binding agents are immobilized on the planar region 110 of the wicking pad, during lateral flow, the binding of the analyte, if present, to the first primary antibody and to the second primary antibody (e.g., detection of the analyte sandwiched between the first and second primary antibodies) is followed visually or by using a detector. In some embodiments, the binding of the analyte to the first and second primary antibodies is visualized and/or detected through the use of detectable moieties and/or labels as described herein.

There are many absorbent bibulous pad materials, wick pad materials, and antibody application materials known in the art, the selection from which can be made to control the volume, to control the flow rate of the system, to ensure even flow, and to ensure complete delivery of antibodies/reagents from the reservoirs. Other methods that affect the timing of reagent/antibody delivery such as using torturous paths in the wick pad are possible. Still other embodiments to control the lateral flow process could be engineered into the support layer where the surface may contain sloped regions to slow or speed the flow of liquid using gravity.

Shown in FIGS. 1-3A are consumable devices that hold a single mini-gel sized membrane. Often users run western blots using membranes termed midi size blots which are typically 2× the width of a mini sized membrane. In other western blot applications the user may cut a mini and/or midi sized membrane into smaller sections that correspond to a few lanes of the original gel used for electrophoresis and transfer of the proteins (e.g., FIG. 4). Therefore, the consumable lateral flow device could be of a size to accommodate either a mini or midi-sized membrane in some embodiments. In still other embodiments there could be separate ridges molded into or otherwise present in the base of the consumable where membrane sections could be placed. In embodiments having a hydrophobic or impermeable barrier (FIG. 5) in the wicking pad, lateral flow zones in the wicking pad can be sized to accommodate mini and/or midi sized membranes or membranes that have been cut into smaller sections.

In other embodiments of the lateral flow device, multiple antibodies may be mixed and loaded into one or more of the reservoirs to facilitate multiplex detection of targets in a single sample.

IV. KITS

Kits for performing a lateral flow assay according to methods described herein are provided. Also provided are kits containing lateral flow devices as described herein. In some embodiments, the kit comprises reagents (e.g., binding agents including labeled primary antibody or primary and secondary antibodies, wash solution, and/or lateral flow buffer) in liquid form (e.g., reagent solutions) that are applied to the device by the end-user. In some embodiments, solutions are provided in a concentrated form, e.g., 5× or 10×) that is diluted prior to use. In some embodiments, the reagents are provided in solid form that is reconstituted with liquid, e.g. buffer, prior to use.

In some embodiments, the kit contains blocking agents (e.g., bovine serum albumin and/or non-fat dried milk), surfactants (e.g., Tween 20 or Triton X-100), protein aggregation modifying agents as described herein, crowding agents (e.g., dextran, polyethylene glycol and/or Ficoll), density agents to control viscosity and fluid flow rate, and/or agents to promote even flow of reagents and/or promote reaction to molecules on the substrate and minimize background on the substrate. The additional agents can be provided in the kit as a solid (e.g., a powder) or in liquid form (e.g., as a solution). In some embodiments, the kit further comprises instructions for carrying out the methods described herein.

IV. EXAMPLE

Example 1

Detection of ERK1/2 and β-Catenin from HeLa Cell Lysate

This example illustrates the use of lateral flow devices as depicted in FIGS. 1A-2B and as described herein to perform western blot assays.

Thermal lamination (FIG. 6A) or pressure sensitive adhesive (FIG. 6B) were used to create the lateral flow laminates used in the testing. A Scotch thermal laminating pouch (3M #TP3854-20) was used to make the thermally sealed device and a clear polypropylene sheet protector was used with a pressure sensitive adhesive (Lohmann GL187) in the second case. Openings were cut into the top sheet of the pouch/protector to create access points for introducing reagents (priAb, Wash1, secAb, Wash2), membrane to be probed, and the dry pump/drain of the lateral flow device. For the reservoirs, slits were 1-4 mm and 9 cm long, for the membrane location 9 cm×8 cm opening, and a 4.5×9 cm opening for the pump. A glass fiber wicking pad (10 cm×26 cm) was sealed all along the outer edge by painting a thin zone of a few millimeters with acrylic polymer (nail polish) to block the voids of the glass fiber in these areas and prevent fluid from flowing out the edges of the wicking pad. The sealed wicking pad was then inserted into the pouch or protector pocket and aligned to the openings on the top face.

In the first case, the Scotch pouch with the aligned wicking pad were fed into a thermal laminating device to heat seal the top and bottom sheets of the pouch around and to the wick material; the heating bonded the glass fiber to the pouch as well. In the second case, pressure sensitive adhesive was applied to the top and bottom plastic sheet protector material and then these were applied to the top and bottom faces of the wick material, encasing it. For reservoirs, rectangular through-holes were cut into a ⅜ inch acrylic sheet and this acrylic block bonded to the top plastic sheet.

Figure 6A:
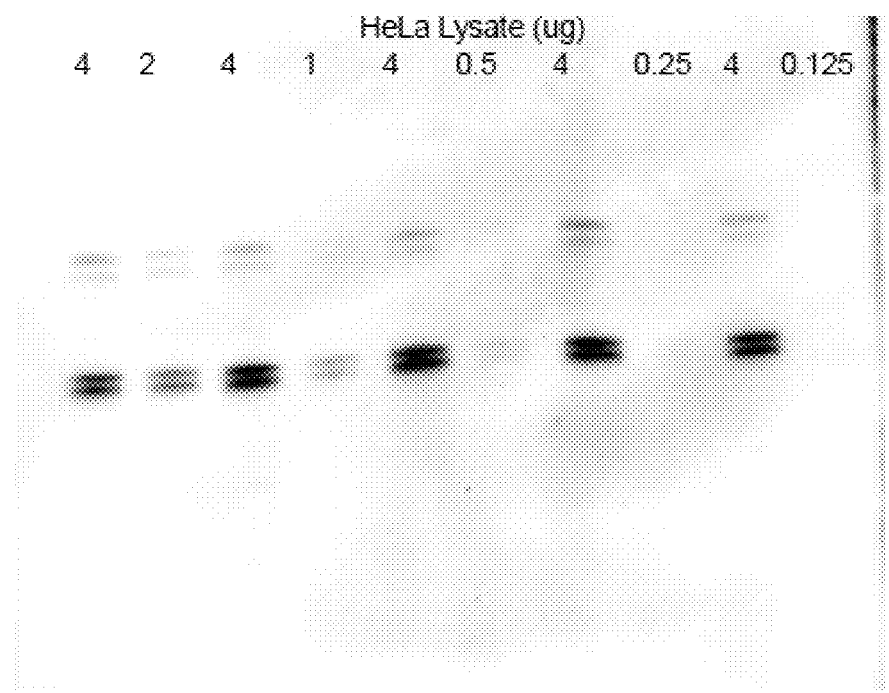
FIGS. 6A and 6B are immunoblotting results using the lateral flow device of FIGS. 1A-2B and as described in Example 1.
Figure 6B:
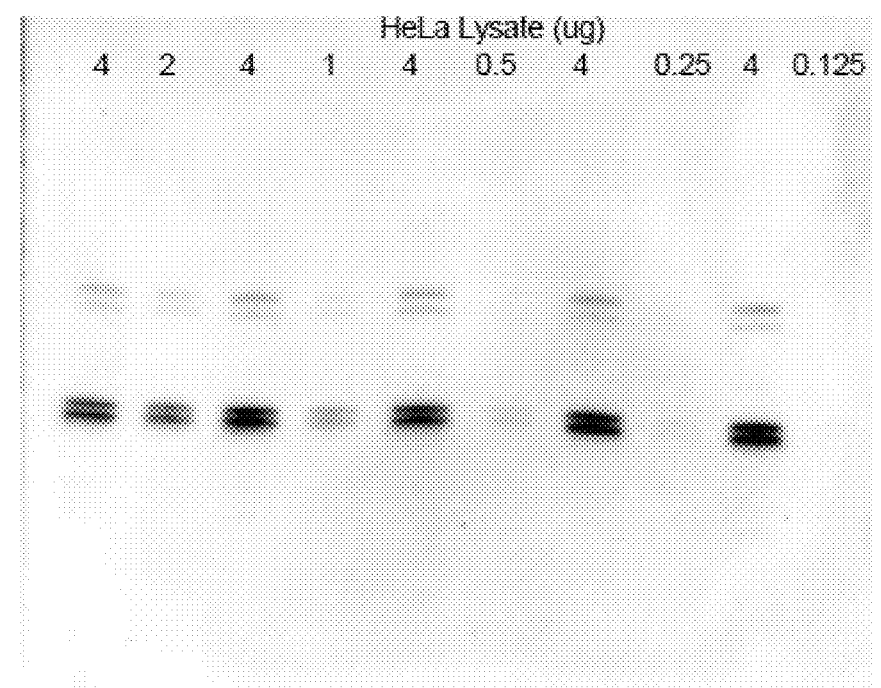

To perform the blot processing, a stack of filter papers was placed in the pump location, the wicking pad was wet with lateral flow (LF) buffer (10 mM phosphate, 150 mM NaCl, pH 7.4, 1% casein, 0.1% Tween 20) by filling the reservoirs and letting the solution wick across to the pump, and then a membrane was loaded protein side down in the membrane zone. Rabbit primary Abs (Cell Signaling Technology), were diluted 1:1000 in LF buffer and loaded (3 ml) into R1. Then 3 ml of LF buffer loaded into R2, 3 ml of secondary Ab goat anti-rabbit IgG-HRP (Bio-Rad STAR-208P) into R3 and 12 ml of LF buffer into R4. After about 4 hr, the membranes were removed, washed 2×3 min in water, and detected with Clarity Chemiluminescence substrate (Bio-Rad). The blots were imaged using a ChemiDoc MP imager (Bio-Rad), with an exposure time of 60 sec. The images in FIGS. 6A and 6B show uniform and sensitive detection of the analytes.

The results show that the lateral flow devices described herein can deliver western blotting reagents (e.g., specific binding agents, lateral flow buffer, wash solutions) sequentially and without user intervention to a blot on a wicking pad.

All patents, patent applications, and other published reference materials cited in this specification are hereby incorporated herein by reference in their entirety.

What is claimed is:

1. A lateral flow device comprising:
   a wicking pad composed of a porous material, the wicking pad having a planar region for contacting a substrate comprising immobilized analytes; and
   wherein the wicking pad has a first end, a second end and two lateral edges;
   a support layer bonded to a first planar surface of the wicking pad;
   a top layer bonded to a second planar surface of the wicking pad, the top layer comprising two or more reservoirs spatially separated from each other, wherein the longitudinal axis of each reservoir is perpendicular to the lateral edges of the wicking pad, wherein each of the reservoirs is in fluid communication with the first end of the wicking pad, and wherein each of the reservoirs comprises an aperture through which a solution is released from the reservoir; and
   a pump comprising an absorbent pad contacting the second end of the wicking pad.

2. The device of claim 1, wherein the aperture is a slot.

3. The device of claim 1, wherein the reservoirs comprise two or more sets of reservoirs spatially separated from and adjacent to each other on the width axis of the lateral flow device.

4. The device of claim 3, wherein the wicking pad further comprises two or more zones separated from each other by a hydrophobic or impermeable barrier that is parallel to the lateral edges of the wicking pad.

5. The device of claim 1, wherein the top layer further comprises a first opening through which the substrate is contacted to the planar region of the wicking pad downstream from the reservoirs.

6. The device of claim 5, wherein the top layer further comprises a second opening through which the pump is contacted to the second planar surface of the wicking pad downstream from the first opening.

7. The device of claim 1, wherein the top layer comprises an opening through which the substrate is contacted to the planar region and through which the pump is contacted to the wicking pad downstream from the planar region.

8. The device of claim 1, wherein the support layer and the top layer are formed from a liquid impermeable material.

9. The device of claim 8, wherein the liquid impermeable material is selected from the group consisting of polypropylene, polycarbonate, polystyrene, polyethylene terephthalate, and polyethylene terephthalate glycol-modified.

10. The device of claim 1, wherein the edges of the wicking pad are sealed with a water-tight material or with a heat seal.

11. The device of claim 10, wherein the water-tight material is selected from the group consisting of acrylic, wax, and photopolymers.

12. The device of claim 1, wherein each of the reservoirs spans a width of the wicking pad.

13. A kit for lateral flow, the kit comprising the device of claim 1.

14. A method of performing a lateral flow assay, the method comprising:
   providing the device of claim 1;
   optionally applying a lateral flow buffer to the wicking pad;
   applying the substrate comprising proteins to the planar region of the wicking pad;
   applying a different reagent solution to each of the reservoirs starting with a reservoir closest to the planar region for applying the substrate; and
   allowing lateral flow of the reagent solutions from the reservoirs to the pump such that each of the reagents in the reagent solutions is sequentially transported in the wicking pad and is contacted to the proteins on the substrate.

15. The method of claim 14, wherein the allowing lateral flow step comprises allowing primary antibodies from a first reagent solution in a first reservoir to bind to target proteins, if present, on the substrate, followed by allowing a first wash solution from a second reagent solution in a second reservoir to remove unbound primary antibodies from the substrate.

16. The method of claim 15, wherein the allowing lateral flow step further comprises allowing secondary antibodies or a secondary detection reagent from a third reagent solution in a third reservoir to contact the primary antibodies bound to target proteins, if present, on the substrate.

17. The method of claim 16, wherein the allowing lateral flow step further comprises allowing a second wash solution from a fourth reagent solution in a fourth reservoir to remove unbound secondary antibodies from the substrate.

18. The method of claim 14, further comprising applying a substantially uniform pressure to the pump.

19. The method of claim 15, further comprising following binding of the primary antibodies to the target proteins if present, optionally following contact of secondary antibodies or secondary detection reagents to the primary antibodies, optionally removing the substrate, and detecting the binding of the primary antibodies to the target proteins if present.

20. The method of claim 14, wherein the different reagent solutions are applied to the reservoirs sequentially.

* * * * *